United States Patent
Moor et al.

(10) Patent No.: US 9,125,373 B2
(45) Date of Patent: Sep. 8, 2015

(54) LETTUCE VARIETY 79-176 RZ

(75) Inventors: Cornelis Marinus Moor, Monster (NL); Egbert Carolus Johannes Smits, Zevenbergen (NL); Hubertus Joseph Wilhelmus Crins, Etten-Leur (NL)

(73) Assignee: RIJK ZWAAN ZAADTEELT EN ZAADHANDEL B.V., De Lier (NL)

( * ) Notice: Subject to any disclaimer, the term of this patent is extended or adjusted under 35 U.S.C. 154(b) by 328 days.

(21) Appl. No.: 13/548,528

(22) Filed: Jul. 13, 2012

(65) Prior Publication Data

US 2013/0019336 A1    Jan. 17, 2013

Related U.S. Application Data

(60) Provisional application No. 61/507,698, filed on Jul. 14, 2011.

(51) Int. Cl.
*A01H 5/12* (2006.01)
(52) U.S. Cl.
CPC .......................................... *A01H 5/12* (2013.01)
(58) Field of Classification Search
None
See application file for complete search history.

(56) References Cited

U.S. PATENT DOCUMENTS 7,371,934 B1 * 5/2008 Skrsyniarz .................... 800/305

OTHER PUBLICATIONS

Enza Zaden catalogue, desdcribing Lettuce 'Blade', 2012-2013.*
IBEB press release "New race of *Bremia lactucae* Bl:27 identified and nominated", May 2010; Plantum NL (Dutch association for breeding, tissue culture, production and trade . . . .
Michelmore R. & Ochoa. O. "Breeding Crisphead Lettuce."In: California Lettuce Research Board, Annual Report 2005-2006, 2006, Salinas, California, pp. 55-68.
Schettini, T.M., Legg, E.J., Michelmore, R.W., 1991. Insensitivity to metalaxyl in California populations of *Bremia lactucae* and resistance of California lettuce cultivars . . . .
Van Ettekoven, K. et al., "Identification and denomination of 'new' races of *Bremia lactucae*," In: Lebeda, A. and Kristkova, E (eds.), Eucarpia Leafy Vegetables, 1999 . . . .
Van der Arend et al. "Identification and denomination of "new" races of *Bremia lactucae* in Europe by IBEB until 2002." In: Van Hintum, Th et al. (eds.), Eucarpia Leafy . . . .

* cited by examiner

*Primary Examiner* — Eileen B O Hara
(74) *Attorney, Agent, or Firm* — Vedder Price P.C.; Thomas J. Kowalski; Deborah L. Lu

(57) ABSTRACT

The present invention relates to a *Lactuca sativa* seed designated 79-176 RZ, which exhibits resistance against downy mildew strains Bl:1-28 and Ca-V to Ca-VIII (*Bremia lactucae*), Nr:0-biotype of *Nasonovia ribisnigri*, and an extraordinary high number of leaves of substantially equal size. The present invention also relates to a *Lactuca* sativa plant produced by growing the 79-176 RZ seed. The invention further relates to methods for producing the lettuce cultivar, represented by lettuce variety 79-176 RZ.

33 Claims, 2 Drawing Sheets

79-176 RZ Fourth Leaf

79-176 RZ Mature Leaf

LETTUCE VARIETY 79-176 RZ

RELATED APPLICATIONS AND INCORPORATION BY REFERENCE

This application claims priority to U.S. provisional patent application Ser. No. 61/507,698 filed Jul. 14, 2011.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

FIELD OF THE INVENTION

The present invention relates to a new lettuce (*Lactuca sativa*) variety which exhibits resistance against downy mildew strains B1:1 to B1:28 (*Bremia lactucae*), currant-lettuce aphid (*Nasonovia ribisnigri*) as well as an extraordinary high number of substantially equally sized leaves.

BACKGROUND OF THE INVENTION

All cultivated forms of lettuce belong to the highly polymorphic species, *Lactuca sativa*, which is grown for its edible head and leaves. As a crop, lettuce is grown commercially wherever environmental conditions permit the production of an economically viable yield.

*Lactuca sativa* is in the Cichoreae tribe of the Asteraceae (Compositae) family. Lettuce is related to chicory, sunflower, aster, scorzonera, dandelion, artichoke and chrysanthemum. *Lactuca sativa* L. is one of about 300 species in the genus *Lactuca*.

Lettuce cultivars are susceptible to a number of pests and diseases such as downy mildew (*Bremia lactucae*). This disease result in millions of dollars of lost lettuce crop throughout the world every year. Downy mildew (*Bremia lactucae*) is highly destructive of lettuce grown at relatively low temperature and high humidity. Downy mildew is caused by a fungus. Downy mildew causes pale, angular, yellow areas bounded by veins on the upper leaf surfaces. Sporulation occurs on the opposite surface of the leaves. The lesions eventually turn brown, and they may enlarge and coalesce. These symptoms typically occur first on the lower leaves of the lettuce, but under ideal conditions may move into the upper leaves of the head. When the fungus progresses to this degree, the head cannot be harvested. Less severe damage requires the removal of more leaves than usual, especially when the lettuce reaches its final destination.

Of the various species of aphids that feed on lettuce, the currant-lettuce aphid (*Nasonovia ribisnigri*) is the most destructive species because it feeds both on the leaves of the lettuce as well as deep in the heart of the lettuce, making it difficult to control with conventional insecticides. The lettuce aphid feeds by sucking sap from the lettuce leaves. Although direct damage to the lettuce may be limited, its infestation has serious consequences because the presence of aphids makes lettuce unacceptable to consumers.

Although several known lettuce cultivars exhibit resistance against disease, irrespective of lettuce type, all the lettuce cultivars affected produce a limited number of leaves that generally are of unequal size and diminished quality with respect to color and shape. This is a distinct disadvantage for processing purposes because leaves either need to be sorted based on size or they need to be cut to a smaller, more uniform size. The first option requires additional labor, with not all sizes usable. The second option has the disadvantage that it creates many cut surfaces, which then are subject to wound-induced browning, resulting in a greatly reduced shelf-life.

Although several known lettuce cultivars produce a large number of small, more uniform leaves (U.S. Pat. No. 6,320,104; US patent publication 20070022496; US patent publication 20100229255), there is a need for a combination of resistance to downy mildew B1:1-28 and Ca-V to Ca-VIII-resistance and currant-lettuce aphid Nr:0.

There exists a need, therefore, for a lettuce variety which exhibits a combination traits including resistance against downy mildew strains B1:1-28 and Ca-V to Ca-VIII (*Bremia lactucae*) and the Nr:0-biotype of *Nasonovia ribisnigri* and an extraordinary high number of leaves of substantially equal size.

Citation or identification of any document in this application is not an admission that such document is available as prior art to the present invention.

SUMMARY OF THE INVENTION

The present invention provides a new type of lettuce (*Lactuca sativa*) variety, designated 79-176 RZ. Lettuce cultivar 79-176 RZ exhibits a combination of traits including resistance against downy mildew strains B1:1-28 and Ca-V to Ca-VIII (*Bremia lactucae*), Nr:0-biotype of *Nasonovia ribisnigri*, and an extraordinary high number of leaves of substantially equal size. Seeds of lettuce cultivar 79-176 RZ have been deposited with the National Collections of Industrial, Marine and Food Bacteria (NCIMB) in Bucksburn, Aberdeen AB21 9YA, Scotland, UK and have been assigned NCIMB Accession No. 41838.

In one embodiment, the invention provides a lettuce plant which may exhibit a combination of traits including resistance against downy mildew strains B1:1-28 and Ca-V to Ca-VIII (*Bremia lactucae*), Nr:0-biotype of *Nasonovia ribisnigri*, and an extraordinary high number of leaves of substantially equal size, representative seed of which have been deposited under NCIMB Accession No. 41838.

In one embodiment, the invention provides a lettuce plant which may exhibit a combination of traits including resistance against downy mildew strains B1:1-28 and Ca-V to Ca-VIII (*Bremia lactucae*), Nr:0-biotype of *Nasonovia ribisnigri*, an extraordinary high number of leaves of substantially equal size, and grayish green bolter leaves with a finely dentate margin, representative seed of which have been deposited under NCIMB Accession No. 41838.

In one embodiment, the invention provides a lettuce plant designated 79-176 RZ, representative seed of which have been deposited under NCIMB Accession No. 41838.

In an embodiment of the present invention, there also is provided parts of a lettuce plant of the invention, which may include parts of a lettuce plant exhibiting a combination of traits including resistance against downy mildew strains B1:1-28 and Ca-V to Ca-VIII (*Bremia lactucae*), Nr:0-biotype of *Nasonovia ribisnigri*, and an extraordinary high number of leaves of substantially equal size, or parts of a lettuce plant having any of the aforementioned resistance(s) and a combination of traits including one or more morphological or physiological characteristics tabulated herein, including parts of lettuce variety 79-176 RZ, wherein the plant parts are involved in sexual reproduction, which include, without limitation, microspores, pollen, ovaries, ovules, embryo sacs or egg cells and/or wherein the plant parts are suitable for vegetative reproduction, which include, without limitation, cuttings, roots, stems, cells or protoplasts and/or wherein the plant parts are tissue culture of regenerable cells in which the cells or protoplasts of the tissue culture are derived from a tissue such as, for example and without limitation, leaves, pollen, embryos, cotyledon, hypocotyls, meristematic cells, roots, root tips, anthers, flowers, seeds or stems. The plants of the invention from which such parts may come from include those wherein representative seed of which has been deposited under NCIMB Accession No. 41838.

In another embodiment there is a plant grown from seeds, representative seed of which having been deposited under NCIMB Accession No. 41838. In a further embodiment there is a plant regenerated from the above-described plant parts or regenerated from the above-described tissue culture. Advantageously such a plant may have morphological and/or physiological characteristics of lettuce variety 79-176 RZ and/or of a plant grown from seed, representative seed of which having been deposited under NCIMB Accession No. NCIMB 41838—including without limitation such plants having all of the morphological and physiological characteristics of lettuce variety 79-176 RZ and/or of plant grown from seed, representative seed of which having been deposited under NCIMB Accession No. NCIMB 41838. Accordingly, in still a further embodiment, there is provided a lettuce plant having all of the morphological and physiological characteristics of lettuce variety 79-176 RZ, representative seed of which having been deposited under NCIMB Accession No. 41838. Such a plant may be grown from the seeds, regenerated from the above-described plant parts, or regenerated from the above-described tissue culture. A lettuce plant having any of the aforementioned resistance(s), and one or more morphological or physiological characteristics recited or tabulated herein, and a lettuce plant advantageously having all of the aforementioned resistances and the characteristics recited and tabulated herein, are preferred. Parts of such plants—such as those plant parts above-mentioned—are encompassed by the invention.

In one embodiment, there is provided progeny of lettuce cultivar 79-176 RZ produced by sexual or vegetative reproduction, grown from seeds, regenerated from the above-described plant parts, or regenerated from the above-described tissue culture of the lettuce cultivar or a progeny plant thereof, representative seed of which having been deposited under NCIMB Accession No. 41838.

Progeny of the lettuce variety 79-176 RZ may be modified in one or more other characteristics, in which the modification is a result of, for example and without limitation, mutagenesis or transformation with a transgene.

In still another embodiment, the present invention provides progeny of lettuce cultivar 79-176 RZ produced by sexual or vegetative reproduction, grown from seeds, regenerated from the above-described plant parts, or regenerated from the above-described tissue culture of the lettuce cultivar or a progeny plant thereof, in which the regenerated plant shows a combination of traits including resistance against downy mildew strains B1:1-28 and Ca-V to Ca-VIII (*Bremia lactucae*), Nr:0-biotype of *Nasonovia ribisnigri*, and an extraordinary high number of leaves of substantially equal size.

In still a further embodiment, the invention may comprise a method of producing a hybrid lettuce seed which may comprise crossing a first parent lettuce plant with a second parent lettuce plant and harvesting the resultant hybrid lettuce seed, in which the first parent lettuce plant or the second parent lettuce plant may be a lettuce plant of the invention, e.g. a lettuce plant having a combination of traits including resistance against downy mildew strains B1:1-28 and Ca-V to Ca-VIII (*Bremia lactucae*), Nr:0-biotype of *Nasonovia ribisnigri*, and an extraordinary high number of leaves of substantially equal size and one or more morphological or physiological characteristics tabulated herein, including a lettuce plant of lettuce cultivar 79-176 RZ, representative seed of which having been deposited under NCIMB 41838.

In another embodiment, the invention may comprise producing a lettuce plant having a combination of traits including resistance against downy mildew strains B1:1-28 and Ca-V to Ca-VIII (*Bremia lactucae*), Nr:0-biotype of *Nasonovia ribisnigri*, and an extraordinary high number of leaves of substantially equal size which may comprise: crossing a mother lettuce plant with a father lettuce plant to produce a hybrid seed; growing said hybrid seed to produce a hybrid plant; selfing said hybrid seed to produce F2 progeny seed; selecting said F2-plants for exhibiting a combination of traits including resistance against downy mildew strains B1:1-28 and Ca-V to Ca-VIII (*Bremia lactucae*), Nr:0-biotype of *Nasonovia ribisnigri*, and an extraordinary high number of leaves of substantially equal size.

Advantageously the selfing and selection may be repeated; for example at least once, or at least twice, thrice, four times, five times, six times or more, to produce F3 or F4 or F5 or F6 or subsequent progeny, especially as progeny from F2 may exhibit the aforementioned combination of traits, and may be desirable.

In still a further embodiment, the invention may comprise a method of producing a lettuce cultivar containing a combination of traits including resistance against downy mildew strains B1:1-28 and Ca-V to Ca-VIII (*Bremia lactucae*), Nr:0-biotype of *Nasonovia ribisnigri*, and an extraordinary high number of leaves of substantially equal size.

The invention even further relates to a method of producing lettuce which may comprise: (a) cultivating to the vegetative plant stage a plant of lettuce variety 79-176 RZ, representative seed of which having been deposited under NCIMB Accession No. NCIMB 41838, and (b) harvesting lettuce leaves or heads from the plant. The invention further comprehends packaging the lettuce plants, heads or leaves.

Accordingly, it is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. §112, first paragraph) or the EPO (Article 83 of the EPC), such that Applicants reserve the right and hereby disclose a disclaimer of any previously described product, process of making the product, or method of using the product.

It is noted that in this disclosure and particularly in the claims, terms such as "comprises", "comprised", and "comprising" and the like (e.g., "includes", "included", "including", "contains", "contained", "containing", "has", "had", "having", etc.) can have the meaning ascribed to them in US Patent law, i.e., they are open ended terms. For example, any method that "comprises," "has" or "includes" one or more steps is not limited to possessing only those one or more steps and also covers other unlisted steps. Similarly, any plant that "comprises," "has" or "includes" one or more traits is not limited to possessing only those one or more traits and covers other unlisted traits. Similarly, the terms "consists essentially of" and "consisting essentially of" have the meaning ascribed to them in US Patent law, e.g., they allow for elements not explicitly recited, but exclude elements that are found in the prior art or that affect a basic or novel characteristic of the invention. See also MPEP §2111.03. In addition, the term "about" is used to indicate that a value includes the standard deviation of error for the device or method being employed to determine the value.

These and other embodiments are disclosed or are obvious from and encompassed by the following Detailed Description.

DEPOSIT

The Deposit with NCIMB Ltd, Ferguson Building, Craibstone Estate, Bucksburn, Aberdeen AB21 9YA, UK, on May 4, 2011, under deposit accession number NCIMB 41838 was made pursuant to the terms of the Budapest Treaty. Upon issuance of a patent, all restrictions upon the deposit will be removed, and the deposit is intended to meet the requirements of 37 CFR §1.801-1.809. The deposit will be maintained in the depository for a period of 30 years, or 5 years after the last request, or for the effective life of the patent, whichever is longer, and will be replaced if necessary during that period.

BRIEF DESCRIPTION OF THE DRAWINGS

The following detailed description, given by way of example, but not intended to limit the invention solely to the specific embodiments described, may best be understood in conjunction with the accompanying drawing, in which.

DETAILED DESCRIPTION OF THE INVENTION

Figure 1:
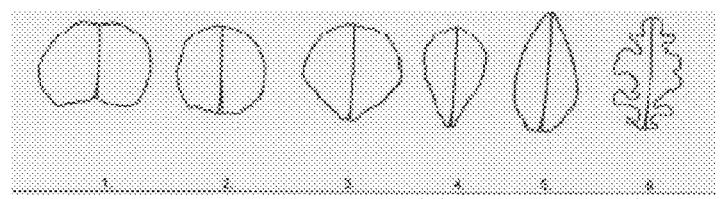
FIG. 1 is an illustration of six different shapes of the fourth leaf from a 20-day old seedling grown under optimal conditions.
Figure 2:
FIG. 2 shows a fourth leaf of 79-176 RZ.
Figure 3:
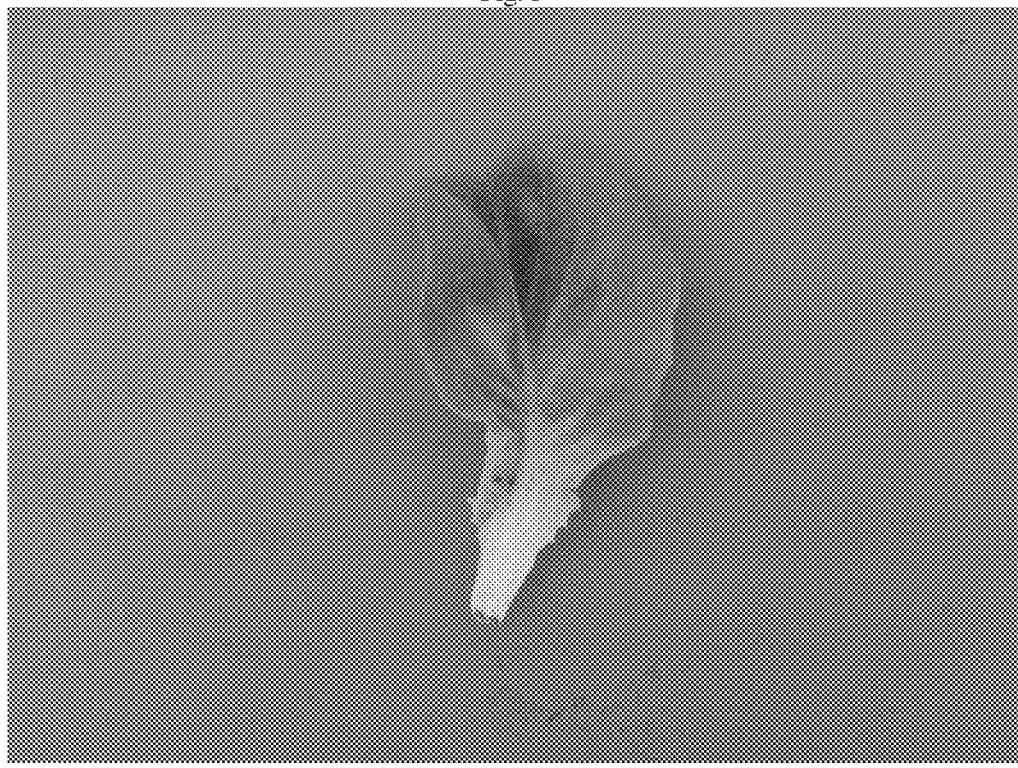
FIG. 3 shows a mature leaf of 79-176 RZ.

The invention provides methods and compositions relating to plants, seeds and derivatives of a new lettuce variety herein referred to as lettuce variety 79-176 RZ. Lettuce variety 79-176 RZ is a uniform and stable line, distinct from other such lines.

In a preferred embodiment, the specific type of breeding method employed for developing a lettuce cultivar is pedigree selection, where both single plant selection and mass selection practices are employed. Pedigree selection, also known as the "Vilmorin system of selection," is described in Fehr, W., Principles of Cultivar Development, Volume I, MacMillan Publishing Co., which is hereby incorporated by reference.

When pedigree selection is applied, in general selection is first practiced among $F_2$ plants. In the next season, the most desirable $F_3$ lines are first identified, and then desirable $F_3$ plants within each line are selected. The following season and in all subsequent generations of inbreeding, the most desirable families are identified first, then desirable lines within the selected families are chosen, and finally desirable plants within selected lines are harvested individually. A family refers to lines that were derived from plants selected from the same progeny from the preceding generation.

Using this pedigree method, two parents may be crossed using an emasculated female and a pollen donor (male) to produce $F_1$ offspring. Lettuce is an obligate self-pollination species, which means that pollen is shed before stigma emergence, assuring 100% self-fertilization. Therefore, in order to optimize crossing, a method of misting may be used to wash the pollen off prior to fertilization to assure crossing or hybridization.

Parental varieties are selected from commercial varieties that individually exhibit one or more desired phenotypes. Additionally, any breeding method involving selection of plants for the desired phenotype may be used in the method of the present invention.

The $F_1$ may be self-pollinated to produce a segregating $F_2$ generation. Individual plants may then be selected which represent the desired phenotype in each generation ($F_3$, $F_4$, $F_5$, etc.) until the traits are homozygous or fixed within a breeding population.

Lettuce variety 79-176 RZ was developed by crossing Archimedes with line 37020 in Fijnaart, The Netherlands, in 2006. The F1 resulting from this cross was grown for seed production in Fijnaart and an F2 plant designated 07P.34759 was selected under glasshouse conditions in 2007. F3 seed was obtained through self-pollination. F3 plant designated 08P.61051 was selected under open field conditions in 2008, Aramon, France, where also F4 seed was produced by selfing the F3 plant. Subsequently, in Daylesford (Australia) the F4 population was sown in plastic tunnels, where plant 08P.101349 was selected, followed by selfing and production of F5 seed. F5 plant 09P.36747 was selected under open field conditions in 2009 in Fijnaart. Finally, a uniform and stable F6 line called 11R.991859 was established and designated as variety 79-176 RZ. This line was multiplied in a glasshouse in Hoek van Holland The Netherlands in 2010 and 2500 seeds were deposited under Accession No. NCIMB 41838 on May 4, 2011.

In one embodiment, a plant of the invention has all the morphological and physiological characteristics of lettuce variety 79-176 RZ. These characteristics of a lettuce plant of the invention, e.g. variety 79-176 RZ, are summarized in Tables 1, 2, and 3.

Next to the morphological and physiological characteristics mentioned in Tables 1, 2, and 3, a plant of the invention also exhibits resistance to downy mildew (*Bremia lactucae* Regel.).

As used herein resistance against *Bremia lactucae* Regel. is defined as the ability of a plant to resist infection by each of the various strains B1:1-28, Ca-V to Ca-VIII of *Bremia lactucae* Regel. in all stages between the seedling stage and the harvestable plant stage. B1:1-28 means strains NL1, NL2, NL4, NL5, NL6, NL7, NL10, NL12, NL13, NL14, NL15, NL16, B1:17, B1:18, B1:20, B1:21, B1:22, B1:23, B1:24, B1:25, B1:26, B1:27, B1:28 (Van Ettekoven K, Van der Arend A J M, 1999. identification and denomination of 'new' races of *Bremia lactucae*. In: Lebeda A, Kristkova E (eds.) Eucarpia leafy vegetables '99. Palacky University, Olomouc, Czech Republic, 1999: 171-175; Van der Arend, A. J. M., Gautier, J., Guenard, M., Michel, H., Moreau, B., de Ruijter, J., Schut, J. W. and de Witte, I. (2003). Identification and denomination of 'new' races of *Bremia lactucae* in Europe by IBEB until 2002. In: Eucarpia leafy vegetables 2003. Proceedings of the Eucarpia Meeting on leafy vegetables genetics and breeding. Noorwijkerhout, The Netherlands. Eds. Van Hintum T., Lebeda A., Pink D., Schut J. pp 151-160; Van der Arend A J M, Gautier J, Grimault V, Kraan P, Van der Laan R, Mazet J, Michel H, Schut J W, Smilde D, De Witte I (2006) Identification and denomination of "new" races of *Bremia lactucae* in Europe by IBEB until 2006; incorporated herein by reference; IBEB press release May 2010; IBEB press release March 2011.

Ca-V to Ca-VIII means Ca-V, Ca-VI, Ca-VII, Ca-VIII (Michelmore R. & Ochoa. O. "Breeding Crisphead Lettuce." In: California Lettuce Research Board, Annual Report 2005-2006, 2006, Salinas, Calif., pp. 55-68).

Resistance typically is tested by two interchangeable methods, described by Bonnier, F. J. M. et al. (Euphytica, 61(3): 203-211, 1992; incorporated herein by reference). One method involves inoculating 7-day old seedlings, and observing sporulation 10 to 14 days later. The other method involves inoculating leaf discs with a diameter of 18 mm obtained from a non-senescent, fully grown true leaf and observing sporulation 10 days later.

As used herein, resistance against Nasonovia ribisnigri (Mosley), or currant-lettuce aphid, is defined as the plant characteristic which results in a non-feeding response of a Nasonovia ribisnigri aphid of the Nr:0-biotype on the leaves of the plant in all stages between 5 true-leaf stage and harvestable plant stage (U.S. Pat. No. 5,977,443 to Jansen, J. P. A., "Aphid Resistance in Composites," p. 12, 1999; incorporated herein by reference).

Resistance is tested by spreading at least ten aphids of biotype Nr:0 on a plant in a plant stage between 5 true leaves and harvestable stage, and observing the density of the aphid population on the plant as well as the growth reduction after 14 days in a greenhouse, with temperature settings of 23 degrees Celsius in daytime and 21 degrees Celsius at night. Day length is kept at 18 hours by assimilation lights.

As used herein, an extraordinary high leaf number is the leaf number of a lettuce plant which is at least about two times to about four times as high as the leaf number of a plant of a regular lettuce variety grown in the same environment during the same period of time. The observation of leaf number should be done at the plant stage where the above-ground dry matter is between 100 and 400 grams and before the plant starts to bolt.

As used herein, a multileaf lettuce plant is a lettuce plant with an extraordinary high leaf number. This is caused by a single recessive genetic factor, which is present in the plant in a homozygous state.

Embodiments of the inventions advantageously have one or more, and most advantageously all, of these characteristics.

In Table 1, the seed color, cotyledon shape and characteristics of the fourth leaf of "79-176 RZ" is compared with "Emerson" and "Grand Rapids".

TABLE 1

| Character | "79-176 RZ" | Emerson | Grand Rapids |
| --- | --- | --- | --- |
| Plant Type | Cutting/leaf | Cutting/leaf | Cutting/leaf |
| Seed Color | Black (Grey brown) | Black (Grey brown) | Black (Grey brown) |
| Cotyledon Shape | Intermediate | Intermediate | Intermediate |
| Shape of Fourth Leaf | Elongated | Elongated | Elongated |
| Rolling of Fourth Leaf | Absent | Absent | Present |
| Cupping of Fourth Leaf | Uncupped | Uncupped | Uncupped |
| Fourth Leaf Apical Margin | Entire | Entire | Slightly dentate |
| Fourth Leaf Basal Margin | Moderately dentate | Moderately dentate | Coarsely dentate |
| Undulation | Flat | Flat | Medium |
| Green color | Medium green | Medium green | Yellow to light green |
| Anthocyanin distribution | Absent | Absent | Absent |

In Table 2, the mature leaf and head characteristics of "79-176 RZ" is compared with "Emerson" and "Grand Rapids".

TABLE 2

| Character | "79-176 RZ" | Emerson | Grand Rapids |
| --- | --- | --- | --- |
| Leaf Color | Medium to dark green | Medium green | Medium to yellow green |
| Anthocyanin Distribution | Absent | Absent | Absent |
| Margin Incision Depth | Absent/shallow | Absent/shallow | Moderate |
| Margin Indentation | Entire | Entire | Moderate |
| Undulations of the Apical Margin | Absent/slight | Absent/slight | Moderate |
| Leaf Size | Small | Small | Medium |
| Leaf Glossiness | Dull | Dull | Moderate |
| Leaf Blistering | Absent/slight | Absent/slight | Strong |
| Leaf Thickness | Thin | Thin | Thin |
| Trichomes | Absent (smooth) | Absent (smooth) | Absent (smooth) |
| Head Shape | Non-heading | Non-heading | Non-heading |
| Butt Shape | Flat | Flat | Rounded |
| Midrib | Moderately raised | Moderately raised | Prominently raised |

In Table 3 the bolting characteristics of "79-176 RZ" is compared with "Emerson" and "Grand Rapids".

TABLE 3

| Character | "79-176 RZ" | Emerson | Grand Rapids |
| --- | --- | --- | --- |
| Bolting class | Slow | Slow | Medium |
| Number of days from first water date to seed stalk emergence | 114 | 118 | 108 |
| Shape bolter leaves | Straight | Straight | Curved |
| Margin bolter leaves | Finely dentate | Dentate | Finely dentate |
| Color bolter leaves | Greyish green | Yellowish green | Light to medium green |
| Terminal inflorescence | Present | Present | Absent |
| Lateral shoots | Absent | Absent | Present |
| Basal side shoots | Present | Present | Present |

In an embodiment, the invention relates to lettuce plants that has all the morphological and physiological characteristics of the invention and have acquired said characteristics by introduction of the genetic information that is responsible for the characteristics from a suitable source, either by conventional breeding, or genetic modification, in particular by cisgenesis or transgenesis. Cisgenesis is genetic modification of plants with a natural gene, coding for an (agricultural) trait, from the crop plant itself or from a sexually compatible donor plant. Transgenesis is genetic modification of a plant with a gene from a non-crossable species or a synthetic gene.

Just as useful traits that may be introduced by backcrossing, useful traits may be introduced directly into the plant of the invention, being a plant of lettuce variety 79-176 RZ, by genetic transformation techniques; and, such plants of lettuce variety 79-176 RZ that have additional genetic information introduced into the genome or that express additional traits by having the DNA coding there for introduced into the genome via transformation techniques, are within the ambit of the invention, as well as uses of such plants, and the making of such plants.

Genetic transformation may therefore be used to insert a selected transgene into the plant of the invention, being a plant of lettuce variety 79-176 RZ or may, alternatively, be used for the preparation of transgenes which may be introduced by backcrossing. Methods for the transformation of plants, including lettuce, are well known to those of skill in the art.

Vectors used for the transformation of lettuce cells are not limited so long as the vector may express an inserted DNA in the cells. For example, vectors which may comprise promoters for constitutive gene expression in lettuce cells (e.g., cauliflower mosaic virus 35S promoter) and promoters inducible by exogenous stimuli may be used. Examples of suitable vectors include pBI binary vector. The "lettuce cell" into which the vector is to be introduced includes various forms of lettuce cells, such as cultured cell suspensions, protoplasts, leaf sections, and callus. A vector may be introduced into lettuce cells by known methods, such as the polyethylene glycol method, polycation method, electroporation, Agrobacterium-mediated transfer, particle bombardment and direct DNA uptake by protoplasts. To effect transformation by electroporation, one may employ either friable tissues, such as a suspension culture of cells or embryogenic callus or alternatively one may transform immature embryos or other organized tissue directly. In this technique, one would partially degrade the cell walls of the chosen cells by exposing them to pectin-degrading enzymes (pectolyases) or mechanically wound tissues in a controlled manner.

A particularly efficient method for delivering transforming DNA segments to plant cells is microprojectile bombardment. In this method, particles are coated with nucleic acids and delivered into cells by a propelling force. Exemplary particles include those comprised of tungsten, platinum, and preferably, gold. For the bombardment, cells in suspension are concentrated on filters or solid culture medium. Alternatively, immature embryos or other target cells may be arranged on solid culture medium. The cells to be bombarded are positioned at an appropriate distance below the macroprojectile stopping plate. An illustrative embodiment of a method for delivering DNA into plant cells by acceleration is the Biolistics Particle Delivery System, which may be used to propel particles coated with DNA or cells through a screen, such as a stainless steel or Nytex screen, onto a surface covered with target lettuce cells. The screen disperses the particles so that they are not delivered to the recipient cells in large aggregates. It is believed that a screen intervening between the projectile apparatus and the cells to be bombarded reduces the size of projectiles aggregate and may contribute to a higher frequency of transformation by reducing the damage inflicted on the recipient cells by projectiles that are too large. Microprojectile bombardment techniques are widely applicable, and may be used to transform virtually any plant species, including a plant of lettuce variety 79-176 RZ.

Agrobacterium-mediated transfer is another widely applicable system for introducing gene loci into plant cells. An advantage of the technique is that DNA may be introduced into whole plant tissues, thereby bypassing the need for regeneration of an intact plant from a protoplast. Agrobacterium transformation vectors are capable of replication in E. coli as well as Agrobacterium, allowing for convenient manipulations. Moreover, advances in vectors for Agrobacterium-mediated gene transfer have improved the arrangement of genes and restriction sites in the vectors to facilitate the construction of vectors capable of expressing various polypeptide coding genes. The vectors have convenient multi-linker regions flanked by a promoter and a polyadenylation site for direct expression of inserted polypeptide coding genes. Additionally, Agrobacterium containing both armed and disarmed Ti genes may be used for transformation. In those plant strains where Agrobacterium-mediated transformation is efficient, it is the method of choice because of the facile and defined nature of the gene locus transfer. The use of Agrobacterium-mediated plant integrating vectors to introduce DNA into plant cells, including lettuce plant cells, is well known in the art (See, e.g., U.S. Pat. Nos. 7,250,560 and 5,563,055).

Transformation of plant protoplasts also may be achieved using methods based on calcium phosphate precipitation, polyethylene glycol treatment, electroporation, and combinations of these treatments.

A number of promoters have utility for plant gene expression for any gene of interest including but not limited to selectable markers, scoreable markers, genes for pest tolerance, disease resistance, nutritional enhancements and any other gene of agronomic interest. Examples of constitutive promoters useful for lettuce plant gene expression include, but are not limited to, the cauliflower mosaic virus (CaMV) P-35S promoter, a tandemly duplicated version of the CaMV 35S promoter, the enhanced 35S promoter (P-e35S), the nopaline synthase promoter, the octopine synthase promoter, the figwort mosaic virus (P-FMV) promoter (see U.S. Pat. No. 5,378,619), an enhanced version of the FMV promoter (P-eFMV) where the promoter sequence of P-FMV is duplicated in tandem, the cauliflower mosaic virus 19S promoter, a sugarcane bacilliform virus promoter, a commelina yellow mottle virus promoter, the promoter for the thylakoid membrane proteins from lettuce (psaD, psaF, psaE, PC, FNR, atpC, atpD, cab, rbcS) (see U.S. Pat. No. 7,161,061), the CAB-1 promoter from lettuce (see U.S. Pat. No. 7,663,027), the promoter from maize prolamin seed storage protein (see U.S. Pat. No. 7,119,255), and other plant DNA virus promoters known to express in plant cells. A variety of plant gene promoters that are regulated in response to environmental, hormonal, chemical, and/or developmental signals may be used for expression of an operably linked gene in plant cells, including promoters regulated by (1) heat, (2) light (e.g., pea rbcS-3A promoter, maize rbcS promoter, or chlorophyll a/b-binding protein promoter), (3) hormones, such as abscisic acid, (4) wounding (e.g., wun1, or (5) chemicals such as methyl jasmonate, salicylic acid, or Safener. It may also be advantageous to employ organ-specific promoters.

Exemplary nucleic acids which may be introduced to the lettuce variety of this invention include, for example, DNA sequences or genes from another species, or even genes or sequences which originate with or are present in lettuce species, but are incorporated into recipient cells by genetic engineering methods rather than classical reproduction or breeding techniques. However, the term "exogenous" is also intended to refer to genes that are not normally present in the cell being transformed, or perhaps simply not present in the form, structure, etc., as found in the transforming DNA segment or gene, or genes which are normally present and that one desires to express in a manner that differs from the natural expression pattern, e.g., to over-express. Thus, the term "exogenous" gene or DNA is intended to refer to any gene or DNA segment that is introduced into a recipient cell, regardless of whether a similar gene may already be present in such a cell. The type of DNA included in the exogenous DNA may include DNA which is already present in the plant cell, DNA from another plant, DNA from a different organism, or a DNA generated externally, such as a DNA sequence containing an antisense message of a gene, or a DNA sequence encoding a synthetic or modified version of a gene.

Many hundreds if not thousands of different genes are known and could potentially be introduced into a plant of lettuce variety 79-176 RZ. Non-limiting examples of particular genes and corresponding phenotypes one may choose to introduce into a lettuce plant include one or more genes for insect tolerance, pest tolerance such as genes for fungal disease control, herbicide tolerance, and genes for quality improvements such as yield, nutritional enhancements, environmental or stress tolerances, or any desirable changes in plant physiology, growth, development, morphology or plant product(s).

Alternatively, the DNA coding sequences may affect these phenotypes by encoding a non-translatable RNA molecule that causes the targeted inhibition of expression of an endogenous gene, for example via antisense- or cosuppression-mediated mechanisms. The RNA could also be a catalytic RNA molecule (i.e., a ribozyme) engineered to cleave a desired endogenous mRNA product. Thus, any gene which produces a protein or mRNA which expresses a phenotype or morphology change of interest is useful for the practice of the present invention. (See also U.S. Pat. No. 7,576,262, "Modified gene-silencing RNA and uses thereof.")

U.S. Pat. Nos. 7,230,158, 7,122,720, 7,081,363, 6,734,341, 6,503,732, 6,392,121, 6,087,560, 5,981,181, 5,977,060, 5,608,146, 5,516,667, each of which, and all documents cited therein are hereby incorporated herein by reference, consistent with the above INCORPORATION BY REFERENCE section, are additionally cited as examples of U.S. patents that may concern transformed lettuce and/or methods of transforming lettuce or lettuce plant cells, and techniques from these US Patents, as well as promoters, vectors, etc., may be employed in the practice of this invention to introduce exogenous nucleic acid sequence(s) into a plant of lettuce variety 79-176 RZ (or cells thereof), and exemplify some exogenous nucleic acid sequence(s) which may be introduced into a plant of lettuce variety 79-176 RZ (or cells thereof) of the invention, as well as techniques, promoters, vectors etc., to thereby obtain further plants of lettuce variety 79-176 RZ, plant parts and cells, seeds, other propagation material harvestable parts of these plants, etc. of the invention, e.g. tissue culture, including a cell or protoplast, such as an embryo, meristem, cotyledon, pollen, leaf, anther, root, root tip, pistil, flower, seed or stalk.

The invention further relates to propagation material for producing plants of the invention. Such propagation material may comprise inter alia seeds of the claimed plant and parts of the plant that are involved in sexual reproduction. Such parts are for example selected from the group consisting of seeds, microspores, pollen, ovaries, ovules, embryo sacs and egg cells. In addition, the invention relates to propagation material which may comprise parts of the plant that are suitable for vegetative reproduction, for example cuttings, roots, stems, cells, protoplasts.

According to a further aspect thereof the propagation material of the invention may comprise a tissue culture of the claimed plant. The tissue culture may comprise regenerable cells. Such tissue culture may be derived from leaves, pollen, embryos, cotyledon, hypocotyls, meristematic cells, roots, root tips, anthers, flowers, seeds and stems. (See generally U.S. Pat. No. 7,041,876 on lettuce being recognized as a plant that may be regenerated from cultured cells or tissue).

Also, the invention comprehends methods for producing a seed of a "79-176 RZ"-derived lettuce plant which may comprise (a) crossing a plant of lettuce variety 79-176 RZ, representative seed of which having been deposited under NCIMB Accession No. NCIMB 41838, with a second lettuce plant, and (b) whereby seed of a "79-176 RZ"-derived lettuce plant form (e.g., by allowing the plant from the cross to grow to producing seed). Such a method may further comprise (c) crossing a plant grown from "79-176 RZ"-derived lettuce seed with itself or with a second lettuce plant to yield additional "79-176 RZ"-derived lettuce seed, (d) growing the additional "79-176 RZ"-derived lettuce seed of step (c) to yield additional "79-176 RZ"-derived lettuce plants, and (e) repeating the crossing and growing of steps (c) and (d) to generate further "79-176 RZ"-derived lettuce plants.

The invention additionally provides a method of introducing a desired trait into a plant of lettuce variety 79-176 RZ which may comprise: (a) crossing a plant of lettuce variety 79-176 RZ, representative seed of which having been deposited under NCIMB Accession No. NCIMB 41838, with a second lettuce plant that may comprise a desired trait to produce F1 progeny; (b) selecting an F1 progeny that may comprise the desired trait; (c) crossing the selected F1 progeny with a plant of lettuce variety 79-176 RZ, to produce backcross progeny; (d) selecting backcross progeny which may comprise the desired trait and the physiological and morphological characteristic of a plant of lettuce variety 79-176 RZ; and, optionally, (e) repeating steps (c) and (d) one or more times in succession to produce selected fourth or higher backcross progeny that comprise the desired trait and all of the physiological and morphological characteristics of a plant of lettuce variety 79-176 RZ, when grown in the same environmental conditions. The invention, of course, includes a lettuce plant produced by this method.

Backcrossing may also be used to improve an inbred plant. Backcrossing transfers a specific desirable trait from one inbred or non-inbred source to an inbred that lacks that trait. This may be accomplished, for example, by first crossing a superior inbred (A) (recurrent parent) to a donor inbred (non-recurrent parent), which carries the appropriate locus or loci for the trait in question. The progeny of this cross are then mated back to the superior recurrent parent (A) followed by selection in the resultant progeny for the desired trait to be transferred from the non-recurrent parent. After five or more backcross generations with selection for the desired trait, the progeny are heterozygous for loci controlling the characteristic being transferred, but are like the superior parent for most or almost all other loci. The last backcross generation would be selfed to give pure breeding progeny for the trait being transferred. When a plant of lettuce variety 79-176 RZ, representative seed of which having been deposited under NCIMB Accession No. NCIMB 41838, is used in backcrossing, offspring retaining the combination of traits including resistance against downy mildew strains B1:1-28 and Ca-V to Ca-VIII (*Bremia lactucae*), Nr:0-biotype of *Nasonovia ribisnigri*, and an extraordinary high number of leaves of substantially equal size. are progeny within the ambit of the invention. Backcrossing methods may be used with the present invention to improve or introduce a characteristic into a plant of the invention, being a plant of lettuce variety 79-176 RZ. See, e.g., U.S. Pat. No. 7,705,206 (incorporated herein by reference consistent with the above INCORPORATION BY REFERENCE section), for a general discussion relating to backcrossing.

The invention further involves a method of determining the genotype of a plant of lettuce variety 79-176 RZ, representative seed of which has been deposited under NCIMB Accession No. NCIMB 41838, or a first generation progeny thereof, which may comprise obtaining a sample of nucleic acids from said plant and detecting in said nucleic acids a plurality of polymorphisms. This method may additionally comprise the step of storing the results of detecting the plurality of polymorphisms on a computer readable medium. The plurality of polymorphisms are indicative of and/or give rise to the expression of the morphological and physiological characteristics of lettuce variety 79-176 RZ.

The polymorphisms of this invention may be provided in a variety of mediums to facilitate use, e.g. a database or computer readable medium, which may also contain descriptive annotations in a form that allows a skilled artisan to examine or query the polymorphisms and obtain useful information.

As used herein "database" refers to any representation of retrievable collected data including computer files such as text files, database files, spreadsheet files and image files, printed tabulations and graphical representations and combinations of digital and image data collections. In a preferred aspect of the invention, "database" refers to a memory system that may store computer searchable information.

As used herein, "computer readable media" refers to any medium that may be read and accessed directly by a computer. Such media include, but are not limited to: magnetic storage media, such as floppy discs, hard disc, storage medium and magnetic tape; optical storage media such as CD-ROM; electrical storage media such as RAM, DRAM, SRAM, SDRAM, ROM; and PROMs (EPROM, EEPROM, Flash EPROM), and hybrids of these categories such as magnetic/optical storage media. A skilled artisan may readily appreciate how any of the presently known computer readable mediums may be used to create a manufacture which may comprise computer readable medium having recorded thereon a polymorphism of the present invention.

As used herein, "recorded" refers to the result of a process for storing information in a retrievable database or computer readable medium. For instance, a skilled artisan may readily adopt any of the presently known methods for recording information on computer readable medium to generate media which may comprise the polymorphisms of the present invention. A variety of data storage structures are available to a skilled artisan for creating a computer readable medium where the choice of the data storage structure will generally be based on the means chosen to access the stored information. In addition, a variety of data processor programs and formats may be used to store the polymorphsims of the present invention on computer readable medium.

The present invention further provides systems, particularly computer-based systems, which contain the polymorphisms described herein. Such systems are designed to identify the polymorphisms of this invention. As used herein, "a computer-based system" refers to the hardware, software and memory used to analyze the polymorphisms. A skilled artisan may readily appreciate that any one of the currently available computer-based system are suitable for use in the present invention.

Lettuce leaves are sold in packaged form, including without limitation as pre-packaged lettuce salad or as lettuce heads. Mention is made of U.S. Pat. No. 5,523,136, incorporated herein by reference consistent with the above INCORPORATION BY REFERENCE section, which provides packaging film, and packages from such packaging film, including such packaging containing leafy produce, and methods for making and using such packaging film and packages, which are suitable for use with the lettuce leaves of the invention. Thus, the invention comprehends the use of and methods for making and using the leaves of the lettuce plant of the invention, as well as leaves of lettuce plants derived from the invention. The invention further relates to a container which may comprise one or more plants of the invention, or one or more lettuce plants derived from a plant of the invention, in a growth substrate for harvest of leaves from the plant in a domestic environment. This way the consumer may pick very fresh leaves for use in salads. More generally, the invention includes one or more plants of the invention or one or more plants derived from lettuce of the invention, wherein the plant is in a ready-to-harvest condition, including with the consumer picking his own, and further including a container which may comprise one or more of these plants.

The invention is further described by the following numbered paragraphs:

1. Lettuce plant exhibiting a combination of traits including resistance against downy mildew strains B1:1-28 and Ca-V to Ca-VIII (*Bremia lactucae*), Nr:0-biotype of *Nasonovia ribisnigri*, and an extraordinary high number of leaves of substantially equal size, representative seed of which having been deposited under NCIMB Accession No. 41838.

2. Lettuce plant exhibiting a combination of traits including resistance against downy mildew strains B1:1-28 and Ca-V to Ca-VIII (*Bremia lactucae*), Nr:0-biotype of *Nasonovia ribisnigri*, an extraordinary high number of leaves of substantially equal size, and grayish green bolter leaves with a finely dentate margin, representative seed of which having been deposited under NCIMB Accession No. 41838.

3. Lettuce plant designated 79-176 RZ, representative seed of which having been deposited under NCIMB Accession No. 41838.

4. A seed of the plant of paragraph 1.

5. Parts of the plant of paragraph 1 or paragraph 2 or paragraph 3, wherein said parts of the plant are suitable for sexual reproduction.

6. Parts of the plant of paragraph 5, said parts selected from the group consisting of microspores, pollen, ovaries, ovules, embryo sacs and egg cells.

7. Parts of the plant of paragraph 1 or paragraph 2 or paragraph 3, wherein said parts of the plant are suitable for vegetative reproduction.

8. Parts of paragraph 7, said parts selected from the group consisting of cuttings, roots, stems, cells and protoplasts.

9. A tissue culture of regenerable cells from the lettuce plant of paragraph 1.

10. A tissue culture of paragraph 9, wherein said cells or protoplasts of the tissue culture which are derived from a tissue selected from the group consisting of leaves, pollen, embryos, cotyledon, hypocotyls, meristematic cells, roots, root tips, anthers, flowers, seeds and stems.

11. Progeny of a lettuce plant of paragraph 1 or paragraph 2 or paragraph 3.

12. Progeny of paragraph 11, wherein said progeny is produced by sexual or vegetative reproduction of said lettuce plant, and wherein said progeny exhibits a combination of traits including resistance against downy mildew strains B1:1-28 and Ca-V to Ca-VIII (*Bremia lactucae*), Nr:0-biotype of *Nasonovia ribisnigri*, and an extraordinary high number of leaves of substantially equal size.

13. Progeny of a lettuce plant of paragraph 3, having all the morphological and physiological characteristics of the lettuce plant of paragraph 3, representative seed of which having been deposited under NCIMB Accession No. 41838 wherein as found in lettuce variety 79-176 RZ, representative seed of which having been deposited under NCIMB Accession No. 41838.

14. Progeny of a lettuce plant of paragraph 1 or paragraph 2 or paragraph 3, representative seed of which having been deposited under NCIMB Accession 41838, and is modified in one or more other characteristics.

15. Progeny of paragraph 14, wherein the modification is effected by mutagenesis.

16. Progeny of paragraph 14, wherein the modification is effected by transformation with a transgene.

17. A method of producing a hybrid lettuce seed comprising crossing a first parent lettuce plant with a second parent lettuce plant and harvesting the resultant hybrid lettuce seed, wherein said first parent lettuce plant or said second parent lettuce plant is the lettuce plant of paragraph 1.

18. A hybrid lettuce plant produced by the method of paragraph 17.

19. A method of producing a lettuce cultivar containing a combination of traits including resistance against downy mildew strains B1:1-28 and Ca-V to Ca-VIII (*Bremia lactucae*), Nr:0-biotype of *Nasonovia ribisnigri*, and an extraordinary high number of leaves of substantially equal size, comprising: crossing a mother lettuce plant with a father lettuce plant to produce a hybrid seed; growing said hybrid seed to produce a hybrid plant; selfing said hybrid seed to produce F2 progeny seed; selecting said F2-plants for exhibiting resistance against downy mildew strains B1:1-28 and Ca-V to Ca-VIII (*Bremia lactucae*), Nr:0-biotype of *Nasonovia ribisnigri*, and an extraordinary high number of leaves of substantially equal size, and, selfing said selected F2-plants to produce F3 progeny seed; selecting F3-plants for exhibiting resistance against downy mildew strains B1:1-28 and Ca-V to Ca-VIII (*Bremia lactucae*), Nr:0-biotype of *Nasonovia ribisnigri*, and an extraordinary high number of leaves of substantially equal size, optionally followed by more selfing and selection steps.

20. A lettuce cultivar produced by the method of paragraph 19.

21. A method for producing lettuce leaves as a fresh vegetable comprising packaging leaves of a plant of paragraph 1.

22. A method for producing lettuce leaves as a processed food comprising processing leaves of a plant of paragraph 1.

23. One or more lettuce plants of paragraph 1, in a container, for harvest of leaves.

24. Lettuce plant having morphological and/or physiological characteristics of a lettuce plant, representative seed of which having been deposited under NCIMB Accession No. 41838.

25. Lettuce plant of paragraph 23 having all the morphological and physiological characteristics of the lettuce plant, representative seed of which having been deposited under NCIMB Accession No. 41838.

26. A method of introducing a desired trait into a plant of lettuce variety 79-176 RZ comprising: (a) crossing a plant of lettuce variety 79-176 RZ, representative seed of which having been deposited under NCIMB Accession No. NCIMB 41838, with a second lettuce plant that comprises the desired trait to produce F1 progeny; (b) selecting an F1 progeny that comprises the desired trait; (c) crossing the selected F1 progeny with a plant of lettuce variety 79-176 RZ, to produce backcross progeny and (d) selecting backcross progeny comprising the desired trait and the physiological and morphological characteristic of a plant of lettuce variety 79-176 RZ, when grown in the same environmental conditions.

27. The method of paragraph 26 further comprising (e) repeating steps (c) and (d) one or more times in succession to produce selected fourth or higher backcross progeny that comprise the desired trait and all of the physiological and morphological characteristics of a plant of lettuce variety 79-176 RZ, when grown in the same environmental conditions.

28. A lettuce plant produced by the method of paragraph 26 or paragraph 27.

29. A method for producing a seed of a 79-176 RZ-derived lettuce plant comprising (a) crossing a plant of lettuce variety 79-176 RZ, representative seed of which having been deposited under NCIMB Accession No. NCIMB 41838, with a second lettuce plant, and (b) whereby seed of a 79-176 RZ-derived lettuce plant form.

30. The method of paragraph 29 further comprising (c) crossing a plant grown from 79-176 RZ-derived lettuce seed with itself or with a second lettuce plant to yield additional 79-176 RZ-derived lettuce seed, (d) growing the additional 79-176 RZ-derived lettuce seed of step (c) to yield additional 79-176 RZ-derived lettuce plants, and (e) repeating the crossing and growing of steps (c) and (d) to generate further 79-176 RZ-derived lettuce plants.

31. Seed produced by the method of paragraphs 29 or 30.

32. A method of determining the genotype of a plant of lettuce variety 79-176 RZ, representative seed of which has been deposited under NCIMB Accession No. NCIMB 41838, or a first generation progeny thereof, comprising obtaining a sample of nucleic acids from said plant and detecting in said nucleic acids a plurality of polymorphisms, wherein the plurality of polymorphisms are indicative of and/or give rise to the expression of the morphological and physiological characteristics of lettuce variety 79-176 RZ.

33. The method of paragraph 32 additionally comprising the step of storing the results of detecting the plurality of polymorphisms on a computer readable medium, or transmitting the results of detecting the plurality of polymorphisms.

34. The computer readable medium of paragraph 33.

Having thus described in detail preferred embodiments of the present invention, it is to be understood that the invention is not to be limited to particular details set forth in the above description as many apparent variations thereof are possible without departing from the spirit or scope of the present invention.

What is claimed is:

1. A lettuce plant exhibiting a combination of traits including resistance against downy mildew strains B1:1-28 and Ca-V to Ca-VIII (*Bremia lactucae*), Nr:0-biotype of *Nasonovia ribisnigri*, and an extraordinary high number of leaves, wherein an extraordinary high leaf number is the leaf number of a lettuce plant which is at least about two times to about four times as high as the leaf number of a plant of a regular lettuce variety grown in the same environment during the same period of time, of substantially equal size, representative seed of which having been deposited under NCIMB Accession No. 41838.

2. A lettuce plant exhibiting a combination of traits including resistance against downy mildew strains B1:1-28 and Ca-V to Ca-VIII (*Bremia lactucae*), Nr:0-biotype of *Nasonovia ribisnigri*, an extraordinary high number of leaves of substantially equal size, wherein an extraordinary high leaf number is the leaf number of a lettuce plant which is at least about two times to about four times as high as the leaf number of a plant of a regular lettuce variety grown in the same environment during the same period of time, and grayish green bolter leaves with a finely dentate margin, representative seed of which having been deposited under NCIMB Accession No. 41838.

3. The lettuce plant designated 79-176 RZ, representative seed of which having been deposited under NCIMB Accession No. 41838.

4. A seed of the plant of claim 1.

5. A part of the plant of claim 1, wherein said part of the plant is suitable for sexual reproduction.

6. The part of the plant as claimed in claim 5, wherein said part comprises a microspore, pollen, ovary, ovule, embryo sac or egg cell.

7. A part of the plant of claim 1, wherein said part of the plant is suitable for vegetative reproduction.

8. The part as claimed in claim 7, wherein said part comprises a cutting, root, stem, cell or protoplast.

9. A tissue culture of regenerable cells or protoplasts from the lettuce plant of claim 1.

10. A tissue culture as claimed in claim 9, wherein said cells or protoplasts of the tissue culture are derived from a tissue comprising a leaf, pollen, embryo, cotyledon, hypocotyl, meristematic cell, root, root tip, anther, flower, seed or stem.

11. A progeny of a lettuce plant of claim 1, wherein the progeny exhibits the combination of traits of the lettuce plant of claim 1.

12. The progeny as claimed in claim 11, wherein said progeny is produced by sexual or vegetative reproduction of said lettuce plant, and wherein said progeny exhibits a combination of traits including resistance against downy mildew strains B1:1-28 and Ca-V to Ca-VIII (*Bremia lactucae*), Nr:0-biotype of *Nasonovia ribisnigri*, and an extraordinary high number of leaves of substantially equal size.

13. A progeny of a lettuce plant of claim 3, having all the morphological and physiological characteristics of the lettuce plant of claim 3 wherein the morphological and physiological characteristics are as found in lettuce variety 79-176 RZ, representative seed of which having been deposited under NCIMB Accession No. 41838.

14. A progeny of a lettuce plant of claim 1, representative seed of which having been deposited under NCIMB Accession 41838, wherein the progeny exhibits the combination of traits of the lettuce plant of claim 1 and wherein the progeny is further modified in one or more other characteristics.

15. The progeny as claimed in claim 14, wherein the modification is effected by mutagenesis.

16. The progeny as claimed in claim 14, wherein the modification is effected by transformation with a transgene.

17. A method of producing a hybrid lettuce seed comprising crossing a first parent lettuce plant with a second parent lettuce plant and harvesting the resultant hybrid lettuce seed, wherein said first parent lettuce plant or said second parent lettuce plant is the lettuce plant of claim 1.

18. A hybrid lettuce seed produced by the method of claim 17, and a hybrid plant grown from said seed.

19. A method of producing a lettuce cultivar containing a combination of traits including resistance against downy mildew strains B1:1-28 and Ca-V to Ca-VIII (*Bremia lactucae*), Nr:0-biotype of *Nasonovia ribisnigri*, and an extraordinary high number of leaves of substantially equal size, wherein an extraordinary high leaf number is the leaf number of a lettuce plant which is at least about two times to about four times as high as the leaf number of a plant of a regular lettuce variety grown in the same environment during the same period of time, representative seed of which having been deposited under NCIMB Accession No. 41838, comprising: crossing a mother lettuce plant with a father lettuce plant to produce a hybrid seed; growing said hybrid seed to produce a hybrid plant; selfing said hybrid seed to produce F2 progeny seed; selecting said F2-plants for exhibiting resistance against downy mildew strains B1:1-28 and Ca-V to Ca-VIII (*Bremia lactucae*), Nr:0-biotype of *Nasonovia ribisnigri*, and an extraordinary high number of leaves of substantially equal size, and, selfing said selected F2-plants to produce F3 progeny seed; selecting F3-plants for exhibiting resistance against downy mildew strains B1:1-28 and Ca-V to Ca-VIII (*Bremia lactucae*), Nr:0-biotype of *Nasonovia ribisnigri*, and an extraordinary high number of leaves of substantially equal size, representative seed of which having been deposited under NCIMB Accession No. 41838, optionally followed by more selfing and selection steps.

20. A lettuce cultivar produced by the method of claim 19.

21. A method for producing lettuce leaves as a fresh vegetable comprising packaging leaves of a plant of claim 1.

22. A method for producing lettuce leaves as a processed food comprising processing leaves of a plant of claim 1.

23. A lettuce plant having the combination of traits of the lettuce plant of claim 1 and other morphological and/or physiological characteristics of a lettuce plant, representative seed of which having been deposited under NCIMB Accession No. 41838.

24. The lettuce plant of claim 23 having all the morphological and physiological characteristics of the lettuce plant, representative seed of which having been deposited under NCIMB Accession No. 41838.

25. A method of introducing a desired trait into a plant of lettuce variety 79-176 RZ comprising: (a) crossing a plant of lettuce variety 79-176 RZ, representative seed of which having been deposited under NCIMB Accession No. NCIMB 41838, with a second lettuce plant that comprises the desired trait to produce F1 progeny; (b) selecting an F1 progeny that comprises the desired trait; (c) crossing the selected F1 progeny with a plant of lettuce variety 79-176 RZ, to produce backcross progeny and (d) selecting backcross progeny comprising the desired trait and physiological and morphological characteristics of a plant of lettuce variety 79-176 RZ, when grown in the same environmental conditions.

26. The method of claim 25 further comprising (e) repeating steps (c) and (d) one or more times in succession to produce selected fourth or higher backcross progeny that comprise the desired trait and all of the physiological and morphological characteristics of a plant of lettuce variety 79-176 RZ, when grown in the same environmental conditions.

27. A lettuce plant produced by the method of claim 25, wherein the lettuce plant comprises the desired trait and the combination of traits of the lettuce plant of claim 1.

28. A method for producing a seed of a 79-176 RZ-derived lettuce plant comprising (a) crossing a plant of lettuce variety 79-176 RZ, representative seed of which having been deposited under NCIMB Accession No. NCIMB 41838, with a second lettuce plant, and (b) whereby seed of a 79-176 RZ-derived lettuce plant form.

29. The method of claim 28 further comprising (c) crossing a plant grown from 79-176 RZ-derived lettuce seed with itself or with a second lettuce plant to yield additional 79-176 RZ-derived lettuce seed, (d) growing the additional 79-176 RZ-derived lettuce seed of step (c) to yield additional 79-176 RZ-derived lettuce plants, and (e) repeating the crossing and growing of steps (c) and (d) to generate further 79-176 RZ-derived lettuce plants.

30. The seed produced by the method of claim 28.

31. A method of determining the genotype of a plant of lettuce variety 79-176 RZ, representative seed of which has been deposited under NCIMB Accession No. NCIMB 41838, or a first generation progeny thereof, comprising obtaining a sample of nucleic acids from said plant and detecting in said nucleic acids a plurality of polymorphisms, wherein the plurality of polymorphisms are indicative of and/or give rise to the expression of the morphological and physiological characteristics of lettuce variety 79-176 RZ.

32. The method of claim 31 additionally comprising the step of storing the results of detecting the plurality of polymorphisms on a computer readable medium, or transmitting the results of detecting the plurality of polymorphisms.

33. A lettuce plant exhibiting a combination of traits including resistance against downy mildew strains B1:1-28 and Ca-V to Ca-VIII (*Bremia lactucae*), Nr:0-biotype of *Nasonovia ribisnigri*, and an extraordinary high number of leaves of substantially equal size, wherein an extraordinary high leaf number is the leaf number of a lettuce plant which is at least about two times to about four times as high as the leaf number of a plant of a regular lettuce variety grown in the same environment during the same period of time, and having genetic information for so exhibiting the combination of traits, wherein the genetic information is as contained in a plant, representative seed of which having been deposited under NCIMB Accession No. 41838.

* * * * *